(12) United States Patent
Chebiyyam et al.

(10) Patent No.: US 6,469,167 B1
(45) Date of Patent: Oct. 22, 2002

(54) PROCESS FOR THE PREPARATION OF THIAZOLIDINE-2,4-DIONE DERIVATIVES

(75) Inventors: Prabhakar Chebiyyam; Rajender Kumar Potlapally; Chinna Bakki Reddy Gade; Balaram Mahanti Satish; Ramabhadra Sarma Mamillapalli; Om Reddy Gaddam, all of Hyderabad (IN)

(73) Assignee: Dr. Reddy's Research Foundation, Andhra Pradesh (IN)

( * ) Notice: Subject to any disclaimer, the term of this patent is extended or adjusted under 35 U.S.C. 154(b) by 0 days.

(21) Appl. No.: 09/763,940
(22) PCT Filed: Sep. 10, 1999
(86) PCT No.: PCT/IB99/01530
 § 371 (c)(1),
 (2), (4) Date: May 2, 2001
(87) PCT Pub. No.: WO00/15638
 PCT Pub. Date: Mar. 23, 2000

(30) Foreign Application Priority Data

Sep. 14, 1998 (IN) ...................................... 2060/MAS/98

(51) Int. Cl.$^7$ ...................... C07D 417/12; C07D 239/88
(52) U.S. Cl. ...................... 544/287; 544/284; 544/298; 544/183; 544/200
(58) Field of Search ................. 544/284, 287, 544/298; 548/183, 200

(56) References Cited

U.S. PATENT DOCUMENTS 5,885,997 A * 3/1999 Lohray et al. ............... 514/256
5,985,884 A * 11/1999 Lohray et al. ............... 514/259

FOREIGN PATENT DOCUMENTS

GB 0306228 * 3/1989
JP 0454501 A2 * 10/1994
JP 0787727 A1 * 1/1996

OTHER PUBLICATIONS

* Reference were mailed with prior office action mailed on Jul. 24, 2001.*

* cited by examiner

Primary Examiner—Floyd D. Higel
Assistant Examiner—Kamal Saeed
(74) Attorney, Agent, or Firm—Ladas & Parry

(57) ABSTRACT

An improved process for the preparation of 5-[4-[[3-Methyl-4-oxo-3,4-dihydroquinazolin-2-yl]methoxy]benzyl]thiazolidine-2,4-dione of formula (1) which comprises: reducing the compound of formula (2') where R represents a $(C_1–C_4)$alkyl group using Raney Nickel or Magnesium in alcohol having 1 to 4 carbon atoms or mixtures thereof, if desired reesterifying using sufphuric acid at a temperature in the range of 0° C. to 60° C. to obtain a compound of formula (3') wherein R is as defined above, hydrolyzing the compound of formula (3') wherein R is as defined above, by conventional methods to obtain the acid of formula (4), condensing the acid of formula (4) with N-methyl anthranilamide directly without any preactivation of the acid to produce the compound of formula (1) and if desired, converting the compound of formula (1) to pharmaceutically acceptable salts thereof by conventional methods.

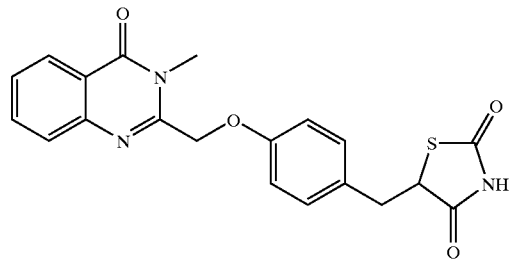

(1)

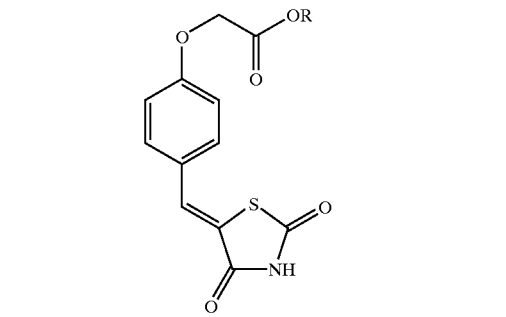

(2')

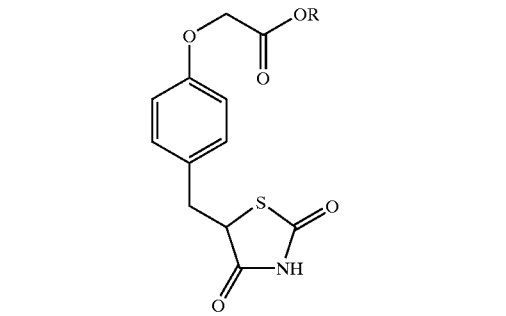

(3')

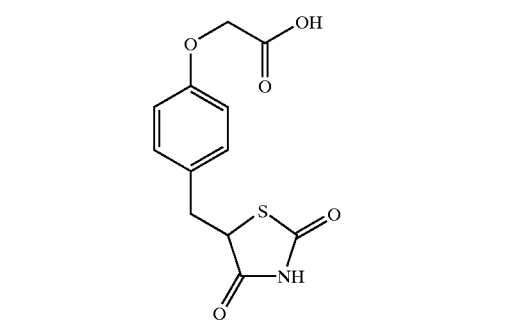

(4)

34 Claims, No Drawings

PROCESS FOR THE PREPARATION OF THIAZOLIDINE-2,4-DIONE DERIVATIVES

FIELD OF INVENTION

The present invention relates to an improved process for the preparation of thiazolidine-2,4-dione derivatives. More particularly the present invention relates to an improved process for the preparation of 5-[4-[[3-Methyl-4-oxo-3,4-dihydroquinazolin-2-yl]methoxy]benzyl]thiazolidine-2,4-dione of the formula (1) and pharmaceutically acceptable salts thereof which are useful as antidiabetic compounds. The thiazolidine-2,4-dione derivative of the formula (1) is particularly useful for the treatment of diabetes type II (NIDDM) and related complications.

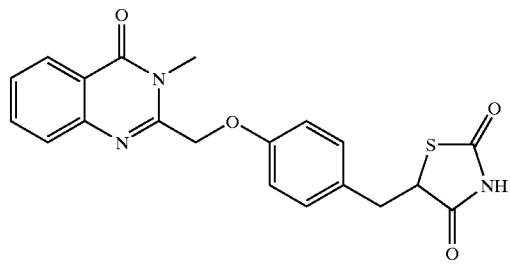

(1)

BACKGROUND OF THE INVENTION

We have in our international publication number WO 97/41097 described the synthesis of the 5-[4-[[3-Methyl-4-oxo-3,4-dihydroquinazolin-2-yl]methoxy]benzyl]thiazolidine-2,4-dione of the formula (1). Compound of the formula (2) on reduction using the expensive catalyst Pd/C in stoichiometric quantity gives the corresponding saturated compound of the formula (3). The ethyl ester of the formula (3) on hydrolysis using methanol/water/sodium carbonate recipe gives the acid of the formula (4) in about 80% yield after a tedious workup sequence involving removal of methanol, then dilution with water, extraction with an organic solvent to remove impurities and then adjustment of pH to precipitate the required acid of the formula (4). The acid of the formula (4) is activated by converting it either to the mixed anhydride of the formula (5) by treating with pivaloyl chloride or the acid chloride of the formula (6) by treating with thionylchloride. Condensation of formula (5) or (6) with N-methyl anthranilamide of the formula (7) gives the amide of the formula (8). Amide of the formula (8) on cyclisation by refluxing in xylene/acetic acid for ~2–30 hours yields about 50% of the cyclised compound of the formula (1). Compound of the formula (1) upon treatment with potassium t-butoxide in methanol gives the corresponding potassium salt of the formula (9). The reaction steps involved in the process are shown in scheme-I below.

Scheme-I

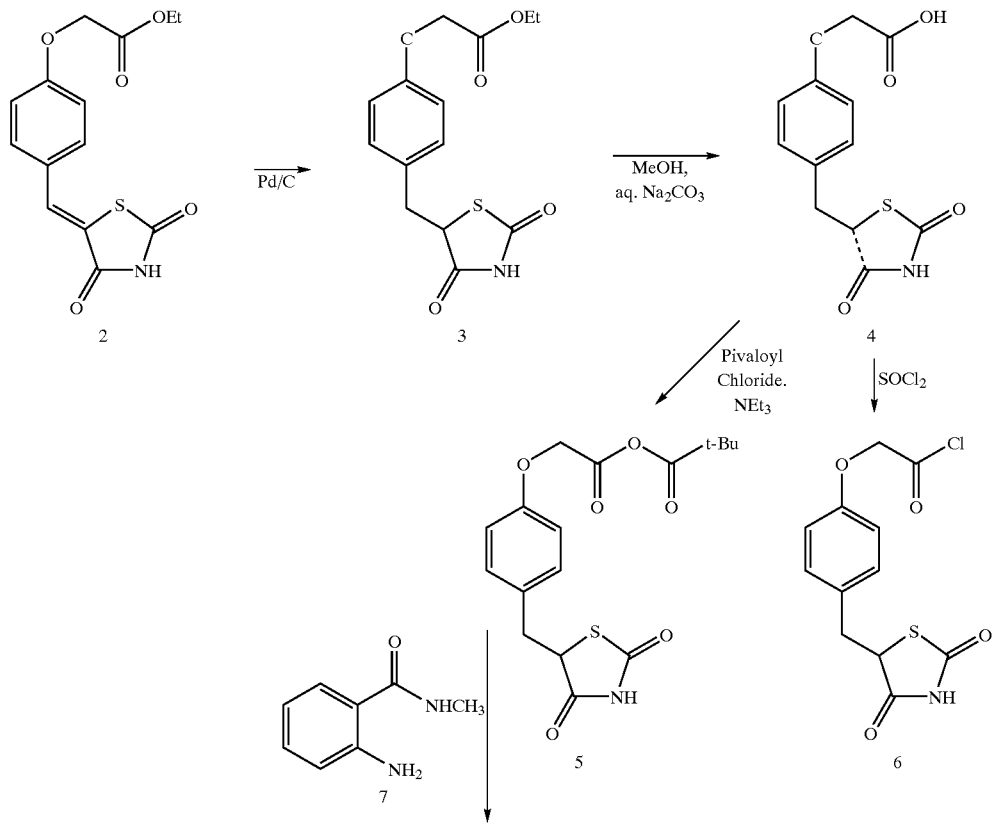

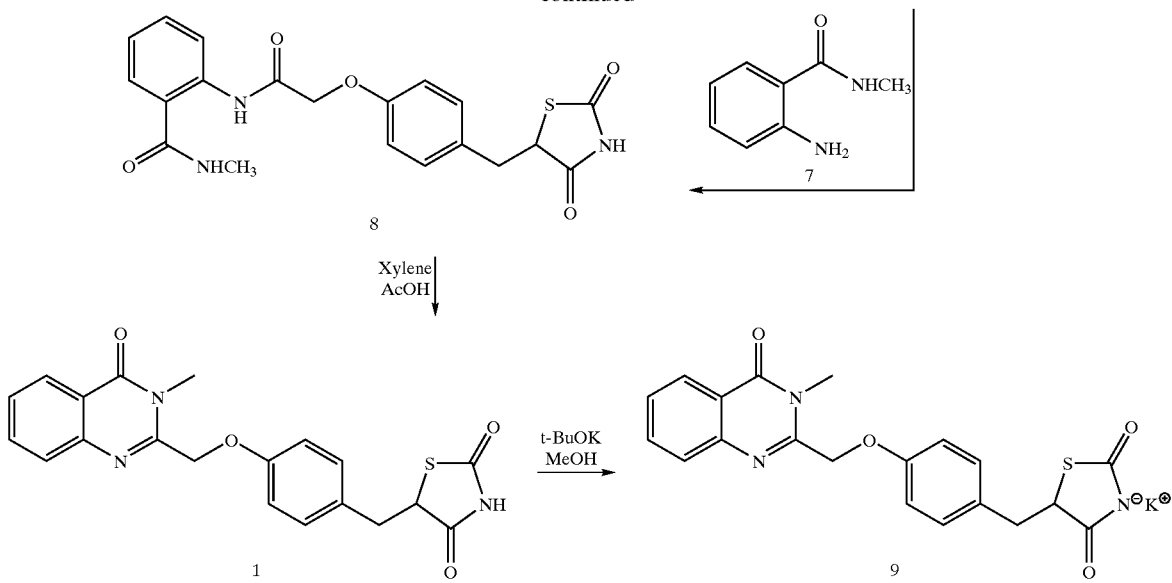

The following are the difficulties encountered during the scaleup trials employing the above said process:

The step of preparing the compound of the formula requires stoichiometric quantities of Pd/C. Nearly 70% of the total cost of the product is due to the use of Pd/C which is very expensive. The time required for the completion of the reaction is about 40 hours, which is also very high and further escalates the cost.

The hydrolysis of compound of formula (3) to give the acid of the formula (4) by using methanol/water/sodium carbonate recipe makes the reaction workup more tedious because it involves removal of methanol, then dilution with water, extraction with an organic solvent to remove impurities and then adjustment of pH to precipitate the required acid of the formula (4), in addition, the reaction time is large, i.e. more than 12 hours. Further the yield is also not very good (80%).

The activation of the acid of the formula (4) by converting to the mixed anhydride of the formula (5) involves use of different chemicals such as pivaloyl chloride, triethylamine and solvents such as dichloromethane, which results in messing-up of the reaction mixture. Further more the conversion of the acid of the formula (4) to the acid chloride of the formula (6) involves the use of corrosive reagents like thionyl chloride. Moreover, the reactions are moisture sensitive.

Because of the large number of chemicals employed in the previous step, the isolation of the intermediate amide of the formula (8) becomes very complicated and also results in low yield (50%) of the amide of the formula (8).

The cyclisation of the intermediate amide of the formula (8) results in low yield (~50%) of the compound of the formula (1) and the reaction time is large (~40 hours)

The preparation of potassium salt of the formula (9) employing potassium t-butoxide is not only risky but also expensive thereby making the process uneconomical.

Keeping in view of the above difficulties in the process disclosed in our copending application mentioned above for the preparation of 5-[4-[[3-Methyl-4-oxo-3,4-dihydroquinazolin-2-yl]methoxy]benzyl]thiazolidine-2,4-dione of the formula (1), we directed our research towards developing an improved process which would be cost and time effective, as well as simple for scaling-up.

OBJECTIVE OF THE INVENTION

The main objective of the present invention is, therefore, to provide an improved process for the preparation of 5-[4-[[3-Methyl-4-oxo-3,4-dihydroquinazolin-2-yl]methoxy]benzyl]thiazolidine-2,4-dione of the formula (1) avoiding the above mentioned difficulties.

Another objective of the present invention is to provide an improved process for the preparation of 5-[4-[[3-Methyl-4-oxo-3,4-dihydroquinazolin-2-yl]methoxy] benzyl] thiazolidine-2,4-dione of the formula (1) without employing expensive and hazardous chemicals thereby making the process not only economical but also safe.

Yet another objective of the present invention is to provide an improved process for the preparation of 5-[4-[[3-Methyl-4-oxo-3,4-dihydroquinazolin-2-yl]methoxy]benzyl] thiazolidine-2,4-dione of the formula (1), which involves very simple work-up procedures making the process simple.

We have developed the improved process of the present invention based on our finding that use of Raney-Nickel or magnesium/methanol as reducing agents to reduce the compound of the formula (2') where R represents a $(C_1-C_4)$alkyl group, not only results in the reduction of cost but also results in efficient reduction. In addition, the compound of formula (3') where R represents a $(C_1-C_4)$alkyl group and the compound of formula (4) can also be directly condensed with N-methyl anthranilamide of the formula (7) without preactivation to produce compound of formula (1) which further makes the process simple and economical.

DETAILED DESCRIPTION OF THE INVENTION

Accordingly the present invention provides an improved process for the preparation of 5-[4-[[3-Methyl-4-oxo-3,4-dihydroquinazolin-2-yl]methoxy]benzyl]thiazolidine-2,4-dione of the formula (1), which comprises:

(a) reducing the compound of the formula (2') where R represents a $(C_1-C_4)$alkyl group using Raney Nickel or Magnesium in alcohol having 1 to 4 carbon atoms or mixtures thereof, and if desired reesterifying using sulphuric acid at a temperature in the range of 0° C. to 60° C. to obtain a compound of formula (3') wherein R is as defined above, (b) hydrolysing the compound of formula (3') wherein R is as defined above, by conventional methods to obtain the acid of the formula (4), (c) condensing the acid of the formula (4) with N-methyl anthranilamide of the formula (7) directly without any pure preactivation of the acid to produce the compound of formula (1) and if desired (d) converting the compound of formula (1) to pharmaceutically acceptable salts thereof by conventional methods.

According to an embodiment of the present invention, the compound of the formula (3') wherein R is as defined above, obtained in step (a) may also be condensed directly with N-methyl anthranilamide of the formula (7) to obtain the compound of the formula (1). The reaction is shown in Scheme-II below:

the formula (3'), in about 85–90% overall yield and a purity of about 97–99%. The reduction using magnesium, (4–12 eq., preferably 8–10 eq.) in alcohol having 1 to 4 carbon atoms or their mixtures at a temperature in the range of 10° C. to 60° C., preferably at a temperature in the range of 15° C. to 30° C. for about 2–15 hours, preferably from 6–8 hours results in a mixture of the acid of the formula (4) and an ester of the formula (3') where R is as defined above.

After reacting with magnesian/alcohol having 1 to 4 carbon atoms for 2–15 hours, preferably from 6–8 hours, either water is added and reaction continued to obtain pure compound of formula (4) or sulphuric acid is added till pH is 2 and refluxed for 2–15 hours, preferably for 6–8 hours to produce pure ester of the formula (3') where R is as defined above. The inorganic salts precipitate out quantitatively in the form of magnesium sulphate. Hence, no dissolved solids get into the effluent. These esters of the formula (3') upon hydrolysis with aq. sodium hydroxide give the acid of the formula (4) in 97–99% yield and 95–99% purity. The reaction time is drastically reduced to only ~2 hours as compared to 12 hours required by the process disclosed in our above said international publication. Workup is also

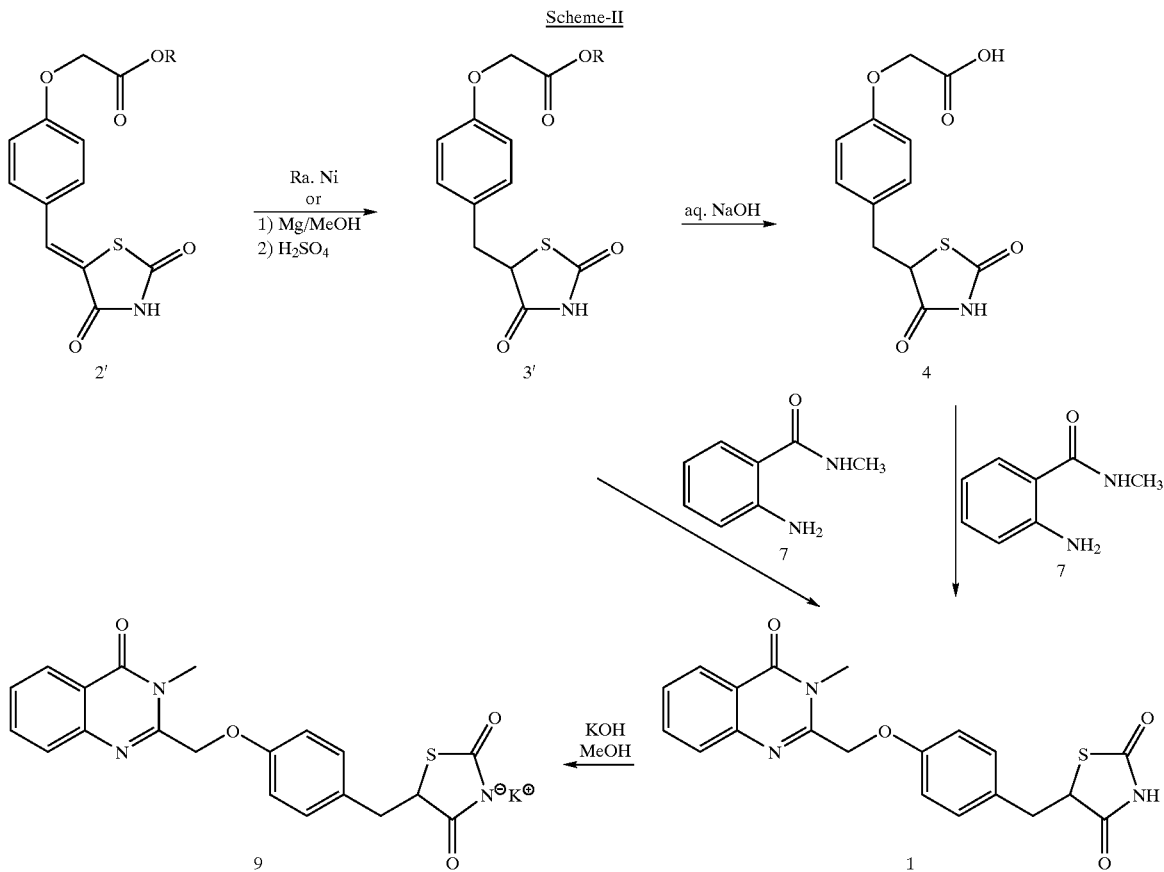

Scheme-II

The reduction of the compound of formula (2') wherein R is as defined above using 40–130% (w/v) preferably 100% (w/v) Raney Nickel proceeds to completion in 8 to 70 hours, preferably from 12–24 hours, at 15° C.–70° C. preferably 30° C.–60° C. and at atmospheric pressure to 600 psi. preferably from atmospheric pressure to 400 psi of hydrogen pressure. The crude material is taken in lower alcohol like methanol, ethanol, propanol and the like and precipitated big adding water thereby affording a highly pure compound of extremely simplified involving only pH adjustment to obtain the required acid of the formula (4). The acid of the formula (4) is condensed with N-methyl anthranilamide of the formula (7) directly for about 6–20 hours, preferably 10–12 hours to produce the compound of formula (1) without any pre-activation of the acid of the formula (4). The yield is ~70% with a purity of ~99%.

Alternatively the condensation can also be carried out with the esters of formula (3') where R is as defined above with N-methyl anthranilamide of the formula (7) for a period of 5–30 hours, preferably 6–20 hours to produce the compound of formula (1) albeit in low yield (20%). However, the yield can be improved to a maximum of 60% if the reaction time is increased to 40–50 hours. The resulting compound of formula (1) upon treating with methanolic potassium hydroxide potassium carbonate or potassium t-butoxide, at 60–70° C. and cooling the reaction mixture to room temperature and maintaining it for 1 h room temperature, (gives the corresponding potassium salt of the formula (9) in ~90% yield in a pharmaceutically acceptable quality. The reaction may be carried out in the presence of solvents such as xylene/methanol mixture in the ration of 1:1. In a similar manner, other pharmaceutically acceptable salts of the formula (1) can be prepared by conventional methods.

The present invention also envisages an improved process for the preparation of compound of the formula (2) starting from p-hydroxybenzaldehyde of the formula (10) and alkyihaloacetate of the formula (11). This process comprises a). reacting p-hydroxybenzaldehyde of the formula (10) and alkylhaloacetate of the formula (11) where Hal represents halogen atom like fluorine, chlorine, bromine or iodine and R is as defined earlier in the presence of aromatic hydrocarbon solvents, a base, alkyl or aryl sulphonic acid and iodine to obtain the compound of the formula (12) where R is as defined earlier.

b). condensing the compound of formula (12) where R is as defined earlier with thiazolidine-2,4-dione of the formula (13) in the presence or absence of a solvent using catalysts to produce a compound of formula (2'). The reaction is shown in Scheme-III below:

Scheme-III

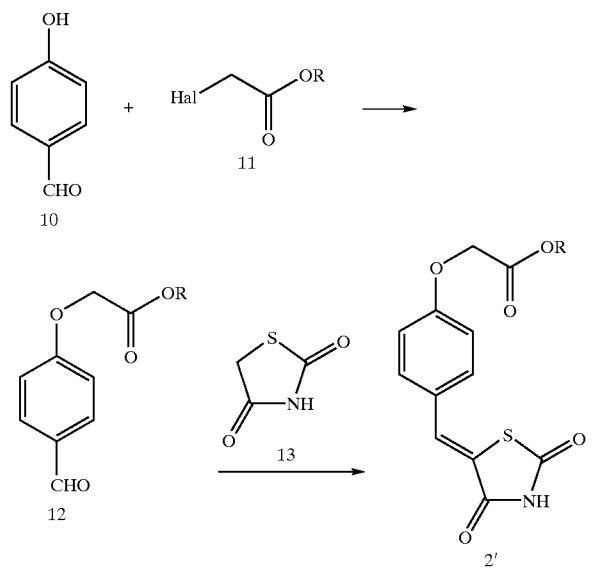

The reaction may be carried out in the presence of aromatic hydrocarbon solvent such as benzene, toluene, xylene and the like or mixtures thereof The base such as alkali and alkaline earth metal carbonates and bicarbonates like potassium carbonate, potassium bicarbonate, sodium carbonate, calcium carbonate and the like may be used. The alkyl or aryl sulphonic acid such as methane sulphonic acid, ethane sulphonic acid, propane sulphonic acid, p-toluene sulphonic acid, benzene sulphonic acid, p-nitro benzene sulphonic acid and the like may be used.

We have observed that the use of iodine activates the halo group present in the compound of formula (11) where Hal represents halogen atom like fluorine, chlorine bromine and R is as defined earlier while reflux using a Dean-Stark condenser in the presence of alkyl or and sulphonic acids helps in enhancing the reaction rate. The reaction is complete in 3–10 hours, preferably 5–7 hours under these conditions as compared to ~18 hours as described in the prior art. Moreover, the reaction workup is simplified by addition of water to the reaction mixture followed by separation of solvent layer. The solvent layer is used as such for the next step of condensing the compound of formula (12) where R is as defined earlier with thiazolidine-2,4-dione of the formula (13). Since, water is being removed azeotropically, in this step, no drying of the solvent layer is required. This process not only uses a single, safe solvent but also optionally makes the two-stage process of the preparation of the compound of formula (12) where R is as defined earlier in a single pot operation. The yield and purity of the compound of the formula (12) is also found to be good (80% and 90% respectively).

The condensation of compound of formula (12) with compound of formula (13) may be carried out in the presence or absence of solvents such as toluene, xylene and the like, using catalysts such as benzoic acid, piperidine and the like, at reflux temperature for a period of 6–8 h to give compound of formula (2') in ~ 85% yield.

The present invention is described in detail with examples given below which are provided by way of illustration only and therefore should not be construed to limit the scope of the invention.

EXAMPLE-1

Preparation of 4-((carboethoxy)methoxy)benzaldehyde

4-Hydroxybenzaldehyde (250 g, 2.05 M), potassium carbonate (565 g, 4.09 M), toluene (2.5 L), p-toluene sulphonic acid (39 g, 0.21 M) and iodine (2 g, catalytic) were taken in a 5 L 4-neck round bottom flask with mechanical stirrer and a Dean-Stark condenser. Ethylbromoacetate (341 g, 2.05 M) was added and the reaction refluxed for 6–8 hours, under azeotropic removal of water, while monitoring the reaction on TLC. After the completion of the reaction, water was added and the organic layer separated while the aq. layer was extracted with toluene (2×500 ml). The combined organic layers were washed with brine and concentrated under vacuum to yield 4-((carboethoxy)methoxy)benzaldehyde as an oily material (407 g, Y=96%, P=99%).

EXAMPLE-2

Alternative Preparation of 4-((carboethoxy)methoxy) benzaldehyde

4-Hydroxybenzaldehyde (250 g, 2.05 M), potassium carbonate (565 g, 4.09 M), toluene (2.5 L), p-toluenesulfonic acid (39 g, 0.21 M) and iodine (2 g, catalytic) were taken in a 5 L 4-neck round bottom flask with mechanical stirrer and a Dean-Stark condenser. Ethylchloroacetate (251 g, 2.05 M) was added and the reaction was refluxed for 6–8 hours, under azeotropic removal of water, while monitoring the reaction on TLC. After the completion of tile reaction, water was added and the organic layer separated while the aq. layer was extracted with toluene (2×500 ml). The combined organic layers were washed with brine and concentrated wider vacuum to yield 4-((carboethoxy)methoxy) benzaldehyde as an oily material (395 g, Y=93%, P=99%).

EXAMPLE-3

Alternative Preparation of 4-((carboethoxy)methoxy)benzaldehyde

4-Hydroxybenzaldehyde (250 g, 2.05 M), potassium carbonate (565 g. 4.09 M), xylene (2.5 L), p-toluenesulfonic acid (39 g, 0.21 M) and iodine (2 g, catalytic) were taken in a 5 L 4-neck round bottom flask with mechanical stirrer and a Dean-Stark condenser. Ethylbromoacetate (341 g, 2.05 M) was added and the reaction was refluxed for 6–8 hours, under azeotropic removal of water while monitoring the reaction on TLC. After the completion of the reaction, water was added and the organic layer separated while the aq. layer was extracted with xylene (2×500 ml). The combined organic layers were washed with brine and concentrated under vacuum to yield 4-((carboethoxy)methoxy)benzaldehyde as an oily material (408 g, Y=97%, P=99%).

EXAMPLE-4

Alternative Preparation of 4-((carboethoxy)methoxy)benzaldehyde

4-Hydroxybenzaldehyde (250 g, 2.05 M), potassium carbonate (565 g, 4.09 M), toluene (2.5 L), methanesulfonic acid (20 g, 0.21 M) and iodine (2 g, catalytic) were taken in a 5 L 4-neck round bottom flask with mechanical stirrer and a Dean-Stark condenser. Ethylbromoacetate (341 g, 2.05 M) was added and the reaction was refluxed for 6–8 hours, under azeotropic removal of water, while monitoring the reaction on TLC. After the completion of the reaction, water was added and the organic layer separated while the aq. layer was extracted with toluene (2×500 ml). The combined organic layers were washed with brine and concentrated under vacuum to yield 4-((carboethoxy)methoxy)benzaldehyde as an oily material (400 g, Y=94%, P=99%).

EXAMPLE-5

Alternative Preparation of 4-((carboethoxy)methoxy)benzaldehyde

4-Hydroxybenzaldehyde (250 g, 2.05 M) potassium carbonate (565 g 4.09 M). toluene (2.5 L), ethanesulfonic acid (23 g, 0.21 M) and iodine (2 g, catalytic) were taken in a 5 L 4-neck round bottom flask with mechanical stirrer and a Dean-Stark condenser. Ethylbromoacetate (341 g, 2.05 M) was added and the reaction was refluxed for 6–8 hours, under azeotropic removal of water, while monitoring the reaction on TLC. After the completion of the reaction, water was added and the organic layer separated while the aq. layer was extracted with toluene (2×500 ml). The combined organic layers were washed with brine and concentrated under vacuum to yield 4-((carboethoxy)methoxy)benzaldehyde as an oily material (395 g, Y=93%, P=99%).

EXAMPLE-6

Preparation of 4-((carbomethoxy)methoxy)benzaldehyde

4-Hydroxybenzaldehyde (250 g, 2.05 M), potassium carbonate (565 g, 4.09 M), toluene (2.5 L), p-toluenesulfonic acid (39 g, 0.21 M) and iodine (2 g, catalytic) were taken in a 5 L 4-neck round bottom flask with mechanical stirrer and a Dean-Stark condenser. Methylbromoacetate (314 g, 2.05 M) was added and the reaction was refluxed for 6–8 hours, under azeotropic removal of water, while monitoring the reaction on TLC. After the completion of the reaction, water was added and the organic layer separated while the aq. layer was extracted with toluene (2×500 ml). The combined organic layers were washed with brine and concentrated under vacuum to yield 4-((carbomethoxy)methoxy)benzaldehyde as an oily material (385 g, Y=97%, P=99%).

EXAMPLE-7

Alternative Preparation of 4-((carbomethoxy)methoxy)benzaldehyde

4-Hydroxybenzaldehyde (250 g, 2.05 M), potassium carbonate (565 g, 4.09 M), toluene (2.5 L), p-toluenesulfonic acid (39 g, 0.21 M) and iodine (2 g, catalytic) were taken in a 5 L 4-neck round bottom flask with mechanical stirrer and a Dean-Stark condenser. Methylchloroacetate (233 g, 2.05 M) was added and the reaction was refluxed for 6–8 hours, under azeotropic removal of water, while monitoring the reaction on TLC. After the completion of the reaction, water was added and the organic layer separated while the aq. layer was extracted with toluene (2×500 ml). The combined organic layers were washed with brine and concentrated under vacuum to yield 4-((carbomethoxy)methoxy)benzaldehyde as an oily material (380 g, Y=95%, P=99%).

EXAMPLE-8

Preparation of 5-[4-[(carboethoxy)methoxy]benzylidine]thiazolidine-2,4-dione 4-((Carboethoxy)methoxy)benzaldehyde obtained by following a procedure described in any of Examples 1–5 (640 g, 3.08 M), thiazolidine-2,4-dione (360 g, 3.08 M), piperidine (45 ml, 0.55 M), benzoic acid (45 g, 0.37 M) and toluene (3 L) were taken in a 5 L 4-neck round bottom flask fitted with a mechanical stirrer and a Dean-Stark condenser. The reaction mixture was refluxed for 6–8 hours, while monitoring the reaction on TLC. After the completion of the reaction, the reaction mass was cooled to 10° C. and the solid thus obtained was filtered, washed with toluene (2×250 ml) and dried at 80° C. for 1–2 hours, to afford 5-[4-[(carboetoxy)methoxy]benzylidine]thiazolidine-2,4-dione (790 g, Y=84%, P=98%).

EXAMPLE-9

Alternative Preparation of 5-[4-[(carboethoxy)methoxy]benzylidine]thiazolidine-2,4-dione 4-((Carboethoxy)methoxy)benzaldehyde obtained by following a procedure described in any of Examples 1–5 (640 g, 3.08 M), thiazolidine-2,4-dione (360 g, 3.08 M), piperidine (45 ml, 0.55 M), benzoic acid (45 g, 0.37 M) and xylene (3 L) were taken in a 5 L 4 neck round bottom flask fitted with a mechanical stirrer and a Dean-Stark condenser. The reaction mixture was refluxed for 6–8 hours, while monitoring the reaction on TLC. After the completion of the reaction, the reaction mass was cooled to 10° C. and the solid thus obtained was filtered, washed with xylene (2×250 ml) and dried at 80° C. for 1–2 hours, to afford 5-[4-[(carboethoxy)methoxy]benzylidine]thiazolidine-2,4-dione (795 g, Y'=85%, P=98%).

EXAMPLE-10

One Pot Preparation of 5-[4-[(carboethoxy)methoxy]benzylidine]thiazolidine-2,4-dione 4-Hydroxybenzaldehyde (250 g, 2.05 M), potassium carbonate (565 g, 4.09 M). toluene (2.5 L), p-toluene sulphonic acid (39 g 0.21 M) and iodine (2 g, catalytic) were taken in a 5 L 4-neck round bottom flask with mechanical stirrer and a Dean-Stark condenser. Ethylbromoacetate (341 g, 2.05 M) was added and the reaction was refluxed for 6–8 hours, under azeotropic removal of water, while monitoring the reaction on TLC. After the completion of the reaction, water was added and the organic layer separated while the aq. layer was extracted with toluene (2×500 ml). The combined organic layers were taken in a 5 L 4-neck round bottom flask fitted with a mechanical stirrer and a Dean-Stark condenser. Thiazolidine-2,4-dione (239 g, 2.05 M), piperidine (30 ml, 0.30 M) and benzoic acid (30 g, 0.20 M) were added and the reaction mixture was refluxed for 6–8 hours, while monitoring the reaction on TLC. After the completion of the reaction, the reaction mass was cooled to 10° C. and the solid thus obtained was filtered, washed with toluene (2×250 ml) and dried at 80° C. for 1–2 hours to afford 5-[4-[(carboethoxy)methoxy]benzylidine]thiazolidine-2,4-dione (473 g, Y=75%, P=98%).

EXAMPLE-11

Alternative One Pot Preparation of 5-[4-[(carboethoxy) methoxy]benzylidine]thiazolidine-2,4-dione 4-Hydroxybenzaldehyde (250 g, 2.05 M), potassium carbonate (565 g, 4.09 M), xylene (2.5 L), p-toluenesulfonic acid (39 g, 0.21 M) and iodine (2 g, catalytic) were taken in a 5 L 4-neck round bottom flask with mechanical stirrer and a Dean-Stark condenser. Ethylbromoacetate (341 g, 2.05 M) was added and the reaction was refluxed for 6–8 hours, under azeotropic removal of water, while monitoring the reaction on TLC. After the completion of the reaction, water was added and the organic layer separated while the aq. layer was extracted with toluene (2×500 ml). The combined organic layer was taken in a 5 L 4-neck round bottom flask fitted with a mechanical stirrer and a Dean-Stark condenser. Thiazolidine-2,4-dione (234 g, 2.00 M), piperidine (30 ml, 0.30 M) and benzoic acid (30 g, 0.20 M) were added and the reaction mixture was refluxed for 6–8 hours, while monitoring the reaction on TLC. After the completion of the reaction, the reaction mass was cooled to 10° C. and the solid thus obtained was filtered, washed with xylene (2×250 ml) and dried at 80° C. for 1–2 hours, to afford 5-[4-[(carboethoxy) methoxy]benzylidine]thiazolidine-2,4-dione (474 g, Y=75%, P=98%).

EXAMPLE-12

Preparation of 5-[4-[(carbomethoxy)methoxy]benzylidine] thiazolidine-2,4-dione 4-((Carbomethoxy)methoxy)benzaldehyde obtained by following a procedure described in Example 6 or 7 (500 g, 2.58 M), thiazolidine-2,4-dione (302 g, 2.58 NM), piperidine (38 ml, 0.46 M), benzoic acid (38 g, 0.31 M) and toluene (3 L) were taken in a 5 L 4-neck round bottom flask fitted with a mechanical stirrer and a Dean-Stark condenser. The reaction mixture was refluxed for 6–8 hours, while monitoring the reaction on TLC. After the completion of the reaction, the reaction mass was cooled to 10° C. and the solid thus obtained was filtered, washed with toluene (2×250 ml) and dried at 80° C. for 1–2 hours, to afford 5-[4-[(carbomethoxy)methoxy]benzylidine]thiazolidine-2,4-dione (645g, Y=85%. P=98%).

EXAMPLE-13

Alternative Preparation of 5-[4-[(carbomethoxy)methoxy] benzylidine]thiazolidine-2,4-dione 4-((Carbomethoxy)methoxy)benzaldehyde obtained by following a procedure described in Example 6 or 7 (500 g, 2.58 M), thiazolidine-2,4-dione (302 g, 2.58 M), piperidine (38 ml, 0.46 M), benzoic acid (38 g, 0.31 M) and xylene (3 L) were taken in a 5 L 4-neck round bottom flask fitted with a mechanical stirrer and a Dean-Stark condenser. The reaction mixture was refluxed for 6–8 hours, while monitoring the reaction on TLC. After the completion of the reaction, the reaction mass was cooled to 10° C. and the solid thus obtained was filtered, washed with xylene (2×250 ml) and dried at 80° C. for 1–2 hours, to afford 5-[4-[(carbomethoxy) methoxy]benzylidine]thiazolidine-2,4-dione (647 g, Y=85%, P=98%).

EXAMPLE-14

One Pot Preparation of 5-[4[(carbomethoxy)methoxy] benzylidine]thiazolidine-2,4-dione 4-Hydroxybenzaldehyde (250 g, 2.05 M), potassium carbonate (565 g, 4.09 M). toluene (2.5 L), p-toluenesulfonic acid (39 g, 0.21 M) and iodine (2 g, catalytic) were taken in a 5 L 4-neck round bottom flask with mechanical stirrer and a Dean-Stark condenser. Methylchloroacetate (223 g, 2.05 M) was added and the reaction was refluxed for 6–8 hours, under azeotropic removal of water, while monitoring the reaction on TLC. After the completion of the reaction, water was added and the organic layer separated while the aq. layer was extracted with 2×500 ml of toluene. The combined organic layers were taken in a 5 L 4 neck round bottom flask fitted with a mechanical stirrer and a Dean-Stark condenser. Thiazolidine-2,4-dione (234 g, 2.00 M), piperidine (30 ml, 0.30 M) and benzoic acid (30 g, 0.20 M) were added and the reaction mixture was refluxed for 6–8 hours, while monitoring the reaction on TLC. After the completion of the reaction, the reaction mass was cooled to 10° C. and the solid thus obtained was filtered, washed with toluene (2×250 ml) and dried at 80° C. for 1–2 hours to afford 5-[4-[(carbomethoxy)methoxy]benzylidine]thiazolidine-2,4-dione (460 g, Y=76%, P=98%).

EXAMPLE-15

Alternative One Pot Preparation of 5-[4-[(carbomethoxy) methoxy]benzylidine]thiazolidine-2,4-dione 4-Hydroxybenzaldehyde (250 g. 2.05 M), potassium carbonate (565 g, 4.09 M), xylene (2.5 L), p-toluenesulfonic acid (39 g, 0.21 M) and iodine (2 g, catalytic) were taken in a 5 L 4-neck round bottom flask with mechanical stirrer and a Dean-Stark condenser. Methylchloroacetate (223 g, 2.05 M) was added and the reaction was refluxed for 6–8 hours, under azeotropic removal of water, while monitoring the reaction on TLC. After the completion of the reaction, water was added and the organic layer separated while the aq. layer was extracted with 2×500 ml of toluene. The combined organic layers were taken in a 5 L 4-neck round bottom flask fitted with a mechanical stirrer and a Dean-Stark condenser. Thiazolidine-2,4-dione (234 g, 2.00 M), piperidine (30 ml, 0.30 M) and benzoic acid (30 g, 0.20 M) were added and the reaction mixture was refluxed for 6–8 hours, while monitoring the reaction on TLC. After the completion of the reaction, the reaction mass was cooled to 10° C. and the solid thus obtained was filtered, washed with xylene (2×250 ml) and dried at 80° C. for 1–2 hours to afford 5-[4-[(carbomethoxy)methoxy]benzylidine]thiazolidine-2,4-dione (465 g, Y=77%, P=98%).

EXAMPLE-16

Preparation of 5-[4-[(carboethoxy)methoxy]benzyl] thiazolidine-2,4-dione

In an autoclave vessel (2 L), Raney Ni (60 ml) was placed along with ethyl acetate (600 ml), after washing the Raney Ni consecutively with water (2×250 ml), methanol (2×150 ml) and ethyl acetate (2×100 ml). Then 5-[4-[(carboethoxy) methoxy]benzylidine]thiazolidine-2,4-dione obtained by following a procedure described in any of Examples 8–11 (100 g, 0.33 M), was charged to the vessel and ethyl acetate (600 ml) added. The mass was kept for hydrogenation at 400 psi hydrogen pressure, at room temperature for 20–30 h and the reaction was monitored on HPLC. After completion of the reaction, the catalyst was filtered and the filtrate was evaporated under reduced pressure to yield an oil. This oil was kept under high vacuum to afford the solid 5-[4-[(carboethoxy)methoxy]benzyl]thiazolidine-2,4-dione in crude form (95–97 g; Yield 94–96%; Purity 86–95%

(HPLC)). Crude 5-[4-[(carboethoxy)methoxy]benzyl] thiazolidine-2,4-dione thus obtained was dissolved in hot methanol (200 ml) and transferred to a 2 L three neck round bottom flask fitted with a mechanical stirrer and liquid addition funnel. Demineralised water (400 ml) was added dropwise to the reaction mixture through the addition funnel, over a period of 30 min. with vigorous stirring during which a white compound precipitated out. Stirring was continued for further 30 min. and second portion of water (200 ml) was added while stirring, over a period of 15 min. to ensure complete precipitation of the product. Stirring was continued for further 1 h. The product was filtered, washed with water (200 ml) and dried under vacuum to yield pure 5-[4-[(carboethoxy)methoxy]benzyl]thiazolidine-2,4-dione (85 g, Y=85%, P=99%).

EXAMPLE-17
Preparation of 5-[4-[(carboethoxy)methoxy]benzyl] thiazolidine-2,4-dione In an autoclave vessel 5-[4-[(carboethoxy)methoxy] benzylidine]thiazolidine-2,4-dione obtained by following a procedure described in any of Examples 8–11 (100 g) and ethyl acetate (600 ml) were placed. Raney Ni (60 ml), pre washed with water (2×100 ml), methanol (2×100 ml) and ethyl acetate (1×100 ml) consecutively, was transferred into the vessel with ethyl acetate (600 ml). Then the mass was kept for hydrogenation at 400 psi hydrogen pressure and room temperature for 24 h. The catalyst was filtered and the filtrate was evaporated and dried over vacuum to obtain 5-[4-[(carboethoxy)methoxy]benzyl]thiazolidine-2,4-dione (98 g, Y=97.3%, P=92%).

EXAMPLE 18
Preparation of 5-[4-[(carboethoxy)methoxy]benzyl] thiazolidine-2,4-dione In an autoclave vessel 5-[4-[(carboethoxy)methoxy] benzylidine]thiazolidine-2,4-dione obtained by following a procedure described in any of Examples 8–11 (100 g) and ethyl acetate (600 ml) were placed. Raney Ni (60 ml), pre-washed with water (2×100 ml), methanol (2×100 ml) and ethyl acetate (1×100 ml) consecutively was transferred into the reaction vessel with ethyl acetate (600 ml). Then the mass was kept for hydrogenation at 200 psi hydrogen pressure and room temperature for 30 h. The catalyst was filtered and the filtrate was evaporated and dried over vacuum to obtain 5-[4[(carboethoxy)methoxy]benzyl] thiazolidine-2,4-dione (100 g, Y=97.35%, P=80%).

EXAMPLE 19
Preparation of 5-[4-[(carboethoxy)methoxy]benzyl] thiazolidine-2,4-dione In an autoclave vessel 5-[4-[(carboethoxy)methoxy] benzylidine]thiazolidine-2,4-dione obtained by following a procedure described in any of Examples 8–11 (100 g) and ethyl acetate (600 ml) were placed. Raney Ni (60 ml) pre-washed with water (2×100 ml), methanol (2×100 ml), ethyl acetate (1×100 ml) consecutively was transferred into the reaction vessel with ethyl acetate (600 ml). Then the mass was kept for hydrogenation at 100 psi hydrogen pressure and room temperature for 70 h. The catalyst was filtered and the filtrate was evaporated and dried over vacuum to obtain 5-[4-[(carboethoxy)methoxy]benzyl] thiazolidine-2,4-dione (100 g, Y=99.35%, P=78%).

EXAMPLE 20
Preparation of 5-[4-[(carboethoxy)methoxy]benzyl] thiazolidine-2,4-dione In an autoclave vessel 5-[4-[(carboethoxy)methoxy] benzylidine]thiazolidine-2,4-dione obtained by following a procedure described in any of Examples 8–11 (40 g) and ethyl acetate (400 ml) were placed. Raney Ni (32 ml) pre-washed wit water (2×100 ml), methanol (2×100 ml), ethyl acetate (1×100 ml) was transferred with ethyl acetate (400 ml) into the vessel. The mass was kept for hydrogenation at 400 psi hydrogen pressure and 50° C.–60° C. temperature for 11 h. The catalyst was filtered and the filtrate was evaporated and dried over vacuum to obtain 5-[4-[(carboethoxy)methoxy]benzyl]thiazolidine-2,4-dione (37 g, Y=92%, 80.17%).

EXAMPLE 21
Preparation of 5-[4-[(carboethoxy)methoxy]benzyl] thiazolidine2,4-dione In a 3 L four necked round bottom flask with a mechanical stirrer, thermometer socket, condenser and a gas sponger, 5-[4-[(carboethoxy)methoxy]benzylidine]thiazolidine-2,4-dione obtained by following a procedure described in any of Examples 8–11 (100 g), ethyl acetate (600 ml) were placed. Raney Ni (100 ml) pre-washed with water (2×150 ml), methanol (2×150 ml), ethyl acetate (1×150 ml) was transferred with ethyl acetate (600 ml) into the vessel. Then hydrogen gas was bubbled into the solution at room temperature for 36 h. The catalyst was filtered and the filtrate was evaporated and dried over vacuum to obtain 5-[4-[(carboethoxy)methoxy]benzyl]thiazolidine-2,4-dione (100 g, Y=99.35%, P=73%)

EXAMPLE-22
Alternative Procedure for the Preparation of 5-[4-[(carboethoxy)methoxy]benzyl]thiazolidine-2,4-dione 5-[4-[(Carboethoxy)methoxy]benzylidine]thiazolidine-2, 4-dione obtained by following a procedure described in any of Examples 8–11 (100 g, 0.33 M), magnesium (95 g, 3.96 M) and methanol (50 ml) were taken into a 5 L round bottom flask fitted with a mechanical stirrer and stirred for 10 minutes at room temperature during which period the magnesium starts reacting, as evinced by effervescence. Ethanol was added and the temperature of the reaction mass was maintained at 20–25° C. for 12 hours, while monitoring the reaction by HPLC. After the complete reduction, the reaction mass was cooled to 5° C. and the pH was adjusted to 2, using conc. sulphuric acid and the reaction mixture was refluxed for a further 12 hours period, while monitoring the reaction by TLC. After complete esterification, the reaction mixture was cooled to room temperature and the magnesium salts (~500 g) were filtered. The filtrate was concentrated under vacuum and the residue was dissolved in ethyl acetate (250 ml) and pure 5-[4-[(carboethoxy)methoxy]benzyl] thiazolidine-2,4-dione was precipitated as a white solid by adding pet, ether (125 ml) followed by stirring at room temperature for 1 hour (59 g, Y=61%, P=97%).

EXAMPLE-23
Preparation of 5-[4-[(carbomethoxy)methoxy]benzyl] thiazolidine-2,4-dione 5-[4-[(Carboethoxy)methoxy]benzylidine]thiazolidine-2, 4-dione obtained by following a procedure described in any of Examples 8–11 (100 g, 0.33 M), magnesium (95 g. 3.96 M) and methanol (2 L) were taken into a 5 L round bottom flask fitted with a mechanical stirrer and stirred for 10 minutes at room temperature during which period the magnesium starts reacting, as evinced by effervescence. The temperature of the reaction mass was maintained at 20–25° C. for 12 hours, while monitoring the reaction by HPLC. After the complete reduction and trans-esterification, the reaction mass was cooled to 5° C. and the pH was adjusted to 2 using conc. sulphuric acid and the reaction mixture was refluxed for a further 12 hours period, while monitoring the reaction by TLC. After complete esterification, the reaction mixture was cooled to room temperature and the magnesium salts (500 g) were filtered. The filtrate was concentrated under vacuum and the residue was dissolved in ethyl acetate (250 ml) and pure 5-[4-[(carbomethoxy)methoxy]benzyl] thiazolidine-2,4-dione was precipitated as a white solid by adding pet, ether (125 ml) followed by stirring at room temperature for 1 hour (60 g ,Y=62%, P=97%).

EXAMPLE-24
Alternative Procedure for the Preparation of 5-[4-[(carbomethoxy)methoxy]benzyl]thiazolidine-2,4-dione 5-[4-[(Carbomethoxy)methoxy]benzylidine]thiazolidine-2,4-dione, obtained by following a procedure described in any of Examples 12–15 (100 g, 0.34 M), magnesium (95 g, 3.96 M) and methanol (2 L) were taken into a 5 L round bottom flask fitted with a mechanical stirrer and stirred for 10 minutes at room temperature during which period the magnesium starts reacting, as evinced by effervescence. The temperature of the reaction mass was maintained at 20–25° C. for 12 hours, while monitoring the reaction by HPLC. After the complete reduction and trans-esterification, the reaction mass was cooled to 5° C. and the pH was adjusted to 2 using conc. sulphuric acid and the reaction mixture was refluxed for a further 12 hours period, while monitoring the reaction by TLC. After complete esterification, the reaction mixture was cooled to room temperature and the magnesium salts (~500 g) were filtered. The filtrate was concentrated under vacuum and the residue was dissolved in ethyl acetate (250 ml) and pure 5-[4-[(carbomethoxy)methoxy]benzyl] thiazolidine-2,4-dione was precipitated as a white solid by adding pet, ether (125 ml) followed by stirring at room temperature for 1 hour (60 g, Y=60%, P=97%).

EXAMPLE-25
Preparation of 5-[4-[(carboxy)methoxy]benzyl]thiazolidine-2,4-dione A suspension of the 5-[4-[(carboethoxy)methoxy]benzyl] thiazolidine-2,4-dione obtained by following a procedure described in any of Examples 16–22 (135 g, 0.44 M) and water (540 ml, 4 times w/v) was taken in a round bottom flask fitted with a mechanical stirrer. Aq. sodium hydroxide solution (37 g of NaOH in 135 ml of water) was added slowly over a period of 5–10 minutes at 20–25° C. Stirring was continued at ambient temperature for a further period of 2–3 h, while monitoring the reaction by TLC. After the completion of reaction, the pH of the reaction mixture was adjusted to 2 using conc. HCl (temp. raises to ~40–45° C.) and allowed to attain room temperature. The mass was cooled to ~10–15° C. and the solid thus obtained was filtered and dried at 60–70° C. under 1–2 mm Hg of vacuum to afford 5-[4-[(carboxy)methoxy]benzyl]thiazolidine-2,4-dione (121 g, Y=99% P=99.2%).

EXAMPLE-26
Alternative Preparation of 5-[4-[(carboxy)methoxy]benzyl] thiazolidine-2,4-dione 5-[4-[(Carboethoxy)methoxy]benzylidine]thiazolidine-2,4-dione, obtained by following a procedure described in any of Examples 8–11 (100 g, 0.33 M), magnesium (95 g, 3.96 M) and methanol (2 L) were taken into a 5 L round bottom flask fitted with a mechanical stirrer and stirred for 10 minutes at room temperature during which period the magnesium starts reacting, as evinced by effervescence. The temperature of the reaction mass was maintained at 20–25° C. for 12 hours, while monitoring the reaction by HPLC. After the complete reduction and trans-esterification, water (2 L) was added to the reaction mass and stirred at ambient temperature for a further 12 hours period, while monitoring the reaction by TLC. After complete hydrolysis, the reaction mixture was acidified to pH 2 and extracted with ethyl acetate (3×200 ml). The combined organic extract was concentrated under vacuum. Pure 5-[4-[(carboxy)methoxy] benzyl]thiazolidine-2,4-dione was precipitated as a white solid by adding pet, ether (125 ml) followed by stirring at room temperature for 1 hour (60 g, Y=66%, P=97%).

EXAMPLE-27
Alternate Procedure for the Preparation of 5-[4-[(carboxy) methoxy]benzyl]thiazolidine-2,4dione A suspension of 5-[4-[(carbomethoxy)methoxy]benzyl] thiazolidine-2,4-dione obtained by following a procedure described in any of Examples 23–24 (135 g, 0.46 M) and water (540 ml, 4 times w/v) was taken in a round bottom flask fitted with a mechanical stirrer. Aq. sodium hydroxide solution (37 g of NaOH in 135 ml of water) was added slowly over a period of 5–10 minutes at 20–25° C. Stirring was continued at ambient temperature for a period of 2–3 h, while monitoring the reaction by TLC. After the completion of the reaction, the pH of the reaction mixture was adjusted to 2 using conc. HCl (temp. raises to 40–45° C.) and allowed to attain room temperature. The mass was cooled to 10–15° C. and the solid thus obtained was filtered and dried at 60–70° C. under 1–2 mm Hg of vacuum to afford 5-[4-[(carboxy)methoxy]benzyl]thiazolidine-2,4-dione (121 g, Y=99%, P=99.2%).

EXAMPLE-28
Alternative Preparation of 5-[4-[(carboxy)methoxy]benzyl] thiazolidine-2,4-dione 5-[4-[(Carbomethoxy)methoxy]benzylidine]thiazolidine-2,4-dione obtained by following a procedure described in any of Examples 12–15 (100 g, 0.34 M). magnesium (95 g, 3.96 M) and methanol (2 L) were taken into a 5 L round bottom flask fitted with a mechanical stirrer and stirred for 10 minutes at room temperature during which period the magnesium starts reacting, as evinced by effervescence. The temperature of the reaction mass was maintained at 20–25° C. for 12 hours, while monitoring the reaction by HPLC. After the complete reduction and trans-esterification, water (2 L) was added to the reaction mass and stirred at ambient temperature for a further 12 hours period while monitoring the reaction by TLC. After complete hydrolysis, the reaction mixture was acidified to pH 2 and extracted with ethyl acetate (3×200 ml). The combined organic extract was concentrated under vacuum. Pure 5-[4-[(carboxy)methoxy] benzyl]thiazolidine-2,4-dione was precipitated as a white solid by adding pet. ether (125 ml) followed by stirring at room temperature for 1 hour (62 g, Y=65%, P=97%).

EXAMPLE-29
Preparation of 5-[4-[[3-Methyl-4-oxo-3,4-dihydroquinazolin-2-yl]methoxy]benzyl]thiazolidine-2,4-dione A suspension of 5-[4-[(carboxy)methoxy]benzyl] thiazolidine-2-4-dione obtained by following a procedure described in any of Examples 25–28 (100 g, 0.356 M), N-methyl anthranilamide (58.7 g, 0.391 M), and p-toluenesulphonic acid (200 mg) was taken in a round bottom flask fitted with a mechanical stirrer, oil bath and Dean-Stark condenser. The reaction mixture was heated to reflux (internal temperature 150–155° C., oil bath temperature 170–180° C.) for a period of 12–15 h while monitoring the reaction by TLC. After completion of the reaction, the reaction mass was cooled to 80° C. and methanol (700 ml)

was added slowly through a dropping funnel. The reaction mass was allowed to attain room temperature while stirring and the solid thus obtained was filtered and washed with methanol (150 ml) and dried at 100–120° C. for 1 h to afford 5-[4-[[3-methyl-4-oxo-3,4-dihydroquinazolin-2-yl]methoxy]benzyl]thiazolidine-2,4-dione as a white solid (100 g, Y=71%, P=98%).

EXAMPLE-30
Alternative Preparation of 5-[4-[[3-methyl-4-oxo-3,4-dihydroquinazolin-2yl]methoxy]benzyl]thiazolidine-2,4-dione A suspension of 5-[4-[(carboxy)methoxy]benzyl]thiazolidine-2,4-dione obtained by following a procedure described in any of Examples 25–28 (100 g., 0.36 M), N-methyl anthranilamide (58.7 g, 0.39 M), xylene (100 ml) and p-toluenesulfonic acid (200 mg) was taken in a round bottom flask fitted with a mechanical stirrer, oil bath and Dean-Stark condenser. The reaction mixture was heated to reflux (Internal temperature 150–155° C., oil bath temperature 170–180° C.) for a period of 12–15 h while monitoring the reaction by TLC. After completion of the reaction, reaction mass was cooled to 80° C. and methanol (700 ml) was added slowly through a dropping funnel. The reaction mass was allowed to attain room temperature while stirring and the solid thus obtained was filtered and washed with methanol (150 ml) and dried at 100–120° C. for 1 h to afford 5-[4-[[3-methyl-4-oxo-3,4-dihydroquinazolin-2-yl]methoxy]benzyl]thiazolidine-2,4-dione as a white solid (95 g, Y=68%, P=98%).

EXAMPLE-31
Alternative Preparation of 5-[4-[[3-methyl-4-oxo-3,4-dihydroquinazolin-2-yl]methoxy]benzyl]thiazolidine-2,4-dione A suspension of 5-[4-[(carbomethoxy)methoxy]benzyl]thiazolidine-2,4-dione (100 g, 0.34 M) obtained in Example 23 or 24, N-methyl anthranilamide (58.7 g, 0.39 M) and p-toluenesulfonic acid (200 mg) was taken in a round bottom flask fitted with a mechanical stirrer, oil bath and Dean-Stark condenser. The reaction mixture was heated to reflux (Internal temperature 150–155° C., oil bath temperature 170–180° C.) for a period of 45–55 h while monitoring the reaction by TLC. After completion of the reaction, the reaction mass was cooled to 80° C. and methanol (700 ml) was added slowly through a dropping funnel. The reaction mass was allowed to attain room temperature while stirring and the solid thus obtained was filtered and washed with methanol (150 ml) and dried at 100–120° C. for 1 h to afford 5-[4-[[3-methyl-4-oxo-3,4-dihydroquinazolin-2-yl]methoxy]benzyl]thiazolidine-2,4-dione as a white solid (71 g, Y=53%, P=98%).

EXAMPLE-32
Alternative Preparation of 5-[4-[[3-methyl-4-oxo-3,4-dihydroquinazolin-2-yl]methoxy]benzyl]thiazolidine-2,4-dione A suspension of 5-[4-[(carbomethoxy)methoxy]benzyl]thiazolidine-2,4-dione obtained by following a procedure described in Example 23 or 24 (100 g, 0.34 M), N-methyl anthranilamide (58.7 g, 0.39 M), xylene (100 ml) and p-toluenesulfonic acid (~200 mg) was taken in a round bottom flask fitted with a mechanical stirrer, oil bath and Dean-Stark condenser. The reaction mixture was heated to reflux (Internal temperature 150–155° C., oil bath temperature 170–180° C.) for a period of 45–55 h while monitoring the reaction by TLC. After completion of the reaction, the reaction mass was cooled to 80° C. and methanol (700 ml) was added slowly through a dropping funnel. The reaction mass was allowed to attain room temperature while stirring and the solid thus obtained was filtered and washed with methanol (150 ml) and dried at 100–120° C. for 1 h to afford 5-[4-[[3-methyl-4-oxo-3,4-dihydroquinazolin-2-yl]methoxy]benzyl]thiazolidine-2,4-dione as a white solid (66 g, Y=49%, P=98%).

EXAMPLE-33
Alternative Preparation of 5-[4-[[3-methyl4-oxo-3,4-dihydroquinazolin-2yl]methoxy]benzyl]thiazolidine-2,4-dione A suspension of 5-[4-[(carboethoxy)methoxy]benzyl]thiazolidine-2,4-dione obtained by following a procedure described in any of Examples 16–22 (100 g, 0.32 M), N-methyl anthranilamide (58.7 g, 0.39 M) and p-toluenesulfonic acid (~200 mg) was taken in a round bottom flask fitted with a mechanical stirrer, oil bath and Dean-Stark condenser. The reaction mixture was heated to reflux (Internal temperature 150–155° C., oil bath temperature 170–180° C.) for a period of 45–55 h while monitoring the reaction by TLC. After completion of the reaction, the reaction mass was cooled to 80° C. and methanol (700 ml) was added slowly through a dropping funnel. The reaction mass was allowed to attain room temperature while stirring and the solid thus obtained was filtered and washed with methanol (150 ml) and dried at 100–120° C. for 1 h to afford 5-[4-[[3-methyl-4-oxo-3,4-dihydroquinazolin-2-yl]methoxy]benzyl]thiazolidine-2,4-dione as a white solid (68 g, Y=53%, P=98%).

EXAMPLE-34
Alternative Preparation of 5-[4-[[3-methyl-4-oxo-3,4-dihydroquinazolin-2-yl]methoxy]benzyl]thiazolidine-2,4-dione A suspension of 5-[4-[(carboethoxy)methoxy]benzyl]thiazolidine-2,4-dione obtained by following a procedure described in any of Examples 16–22 (100 g, 0.32 M), N-methyl anthranilamide (58.7 g, 0.39 M), xylene (100 ml) and p-toluenesulfonic acid (~200 mg) was taken in a round bottom flask fitted with a mechanical stirrer, oil bath and Dean-Stark condenser. The reaction mixture was heated to reflux (Internal temperature 150–155° C., oil bath temperature 170–180° C.) for a period of 45–55 h while monitoring the reaction by TLC. After completion of the reaction, the reaction mass was cooled to 80° C. and methanol (700 ml) was added slowly through a dropping funnel. The reaction mass was allowed to attain room temperature while stirring and the solid thus obtained was filtered and washed with methanol (150 ml) and dried at 100–120° C. for 1 h to afford 5-[4-[[3-methyl-4-oxo-3,4-dihydroquinazolin-2-yl]methoxy]benzyl]thiazolidine-2,4-dione as a white solid (62 g, =48%, P=98%).

EXAMPLE-35
Alternative Preparation of 5-[4-[[3-methyl-4-oxo-3,4-dihydroquinazolin-2yl]methoxy]benzyl]thiazolidine-2,4-dione A suspension of 5-[4-[(carboethoxy)methoxy]benzyl]thiazolidine-2,4-dione obtained by following a procedure described in any of Examples 16–22 (100 g, 0.32 M), N-methyl anthranilamide (58.7 g, 0.39 M) and p-toluenesulfonic acid (200 mg) was taken in a round bottom flask fitted with a mechanical stirrer, oil bath and Dean-Stark condenser. The reaction mixture was heated to reflux (Internal temperature 150–155° C., oil bath temperature 170–180° C.) for a period of 10–15 h while monitoring the reaction by TLC. After completion of the reaction, the reaction mass was cooled to 80° C. and methanol (700 ml) was added slowly through a dropping funnel. The reaction mass was allowed to attain room temperature while stirring and the solid thus obtained was filtered and washed with methanol (150 ml) and dried at 100–120° C. for 1 h to afford 5-[4-[[3-methyl-4-oxo-3,4-dihydroquinazolin-2-yl] methoxy]benzyl]thiazolidine-2,4-dione as a white solid (29 g, Y=23%, P=98%).

EXAMPLE-36
Alternative Preparation of 5-[4-[[3-methyl-4-oxo-3,4-dihydroquinazolin-2-yl]methoxy]benzyl]thiazolidine-2,4-dione A suspension of 5-[4-[(carboethoxy)methoxy]benzyl] thiazolidine-2,4-dione obtained by following a procedure described in any of Examples 16–22 (100 g, 0.32 M), N-methyl anthranilamide (58.7 g, 0.39 M), xylene (100 ml) and p-toluenesulfonic acid (200 mg) was taken in a round bottom flask fitted with a mechanical stirrer, oil bath and Dean-Stark condenser. The reaction mixture was heated to reflux (Internal temperature 150–155° C., oil bath temperature 170–180° C.) for a period of 10–15 h while monitoring the reaction by TLC. After completion of the reaction, the reaction mass was cooled to 80° C. and methanol (700 ml) was added slowly through a dropping funnel. The reaction mass was allowed to attain room temperature while stirring and the solid thus obtained was filtered and washed with methanol (150 ml) and dried at 100–120° C. for 1 h to afford 5-[4-[[3-methyl-4-oxo-3,4-dihydroquinazolin-2-yl] methoxy]benzyl]thiazolidine-2,4-dione as a white solid (29 g, Y-23%, P=98%)

EXAMPLE-37
Alternative Preparation of 5-[4-[[3-methyl-4-oxo-3,4-dihydroquinazolin-2-yl]methoxy]benzyl]thiazolidine-2,4-dione A suspension of 5-[4-[(carbomethoxy)methoxy]benzyl] thiazolidine-2,4-dione obtained by following a procedure described in Examples 23 or 24 (100 g, 0.34 M), N-methyl anthranilamide (58.7 g, 0.39 M) and p-toluenesulfonic acid (~200 mg) was taken in a round bottom flask fitted with a mechanical stirrer, oil bath and Dean-Stark condenser. The reaction mixture was heated to reflux (Internal temperature 150–155° C. oil bath temperature 170–180° C.) for a period of 10–15 h while monitoring the reaction by TLC. After completion of the reaction, reaction mass was cooled to 80° C. and methanol (700 ml) was added slowly through a dropping funnel. The reaction mass was allowed to attain room temperature while stirring and the solid thus obtained was filtered and washed with methanol (150 ml) and dried at 100–120° C. for 1 h to afford 5-[4-[[-methyl-4-oxo-3,4-dihydroquinazolin-2-yl]methoxy]benzyl]thiazolidine-2,4-dione as a white solid (28 g, Y=23%, P=98%).

EXAMPLE-38
Alternative Preparation of 5-[4-[[3-Methyl-4-oxo-3,4-dihydroquinazolin-2-yl]methoxy]benzyl]thiazolidine-2,4-dione A suspension of 5-[4-[(carbomethoxy)methoxy]benzyl] thiazolidine-2,4-dione obtained by following a procedure described in Examples 23 or 24 (100 g, 0.34 M), N-methyl anthranilamide (58.7 g, 0.39 M), xylene (100 ml) and p-toluenesulfonic acid (200 mg) was taken in a round bottom flask fitted with a mechanical stirrer, oil bath and Dean-Stark condenser. The reaction mixture was heated to reflux (internal temperature 150–155° C., oil bath temperature 170–180° C.) for a period of 10–15 h while monitoring the reaction by TLC. After completion of the reaction, reaction mass was cooled to 80° C. and methanol (700 ml) was added slowly through a dropping funnel. The reaction mass was allowed to attain room temperature while stirring and the solid thus obtained was filtered and washed with methanol (150 ml) and dried at 100–120° C. for 1 h to afford 5-[4-[[3-methyl-4-oxo-3,4-dihydroquinazolin-2-yl] methoxy]benzyl]thiazolidine-2,4-dione as a white solid (30 g, Y=23%, P=98%).

EXAMPLE-39
Preparation of 5-[4-[[3-methyl-4-oxo-3,4-dihydroquinazolin-2yl]methoxy]benzyl]thiazolidine-2,4-dione potassium salt 5-[4-[[3-Methyl-4-oxo-3,4-dihydroquinazolin-2-yl] methoxy]benzyl]thiazolidine-2,4dione obtained by following a procedure described in any of Examples 29–38 (100 g, 0.25 M) was dissolved in 1 L of xylene: MeOH (1:1) mixture at 80–90° C., treated with decolourising carbon (20 g) and filtered. To the filtrate was added potassium hydroxide solution (15.6 g of potassium hydroxide dissolved in 200 ml of methanol) slowly over a period of 5–10 min. at 60–70° C. Stirring was continued at ambient temperature for a period of 1 h. The solid obtained was filtered, washed with methanol (300 ml) and dried at 120° C. for I b to yield 5-[4-[[3-methyl-4-oxo-3,4-dihydroquinazolin-2-yl]methoxy]benzyl] thiazolidine-2,4-dione potassium salt as an off-white solid (98 g, Y=89%, P=99.5%).

EXAMPLE-40
Alternative Preparation of 5-[4-[[3-methyl-4-oxo-3,4-dihydroquinazolin-2-yl]methoxy]benzyl]thiazolidine-2,4-dione potassium salt 5-[4-[[3-methyl-4-oxo-3,4-dihydroquinazolin-2-yl] methoxy]benzyl]thiazolidine-2,4-dione obtained by following a procedure described in any of Examples 29–38 (100 g, 0.25 M) was dissolved in 1 L of xylene: MeOH (1:1) mixture at 80–90° C. treated with decolourising carbon (20 g) and filtered. To the filtrate was added potassium t-butoxide solution (31.56 g of potassium t-butoxide dissolved in 200 ml of methanol) slowly over a period of 5–10 min. at 60–70° C. Stirring was continued at ambient temperature for a period of 1 h. The solid obtained was filtered, washed with methanol (300 ml) and dried at 120° C. for 1 h to yield 5-[4-[[3-methyl-4-oxo-3,4-dihydroquinazolin-2-yl] methoxy]benzyl]thiazolidine-2,4-dione potassium salt as a white solid (100 g, Y=91%. P=99.6%).

Advantages of the Invention

The process is simple and economical.

Multisolvent systems are replaced with single solvent system.

Use of expensive Pd/C for reduction is replaced with relatively inexpensive reagents like Raney Nickel or Magnesium/alcohol having 1 to 4 carbon atoms.

Activation of the acid prior to condensation with N-methyl anthranilamide is avoided. Direct condensation is easier to handle as the reaction is insensitive to moisture.

Expensive and hazardous potassium t-butoxide for potassium salt formation is replaced with potassium hydroxide.

We claim:

1. A process for the preparation of 5-[4-[[3-methyl-4-oxo-3,4-dihydroquinazolin-2-yl]methoxy]benzyl]thiazolidine-2,4-dione of the formula (1)

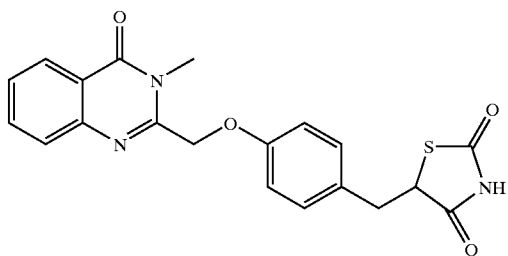

which comprises:

a) reducing the compound of formula (2')

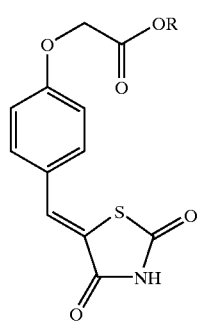

where R represents a ($C_1$–$C_4$)alkyl group using Raney nickel or magnesium and optionally reesterifying rising sulphuric acid at a temperature in the range of 0° C. to 60° C. to obtain a compound of formula (3')

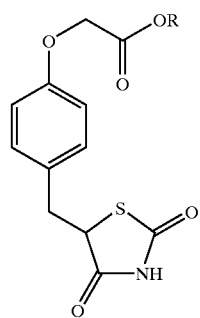

wherein R is as defined above, b) hydrolyzing the compound of formula (3') to obtain the acid of the formula (4),

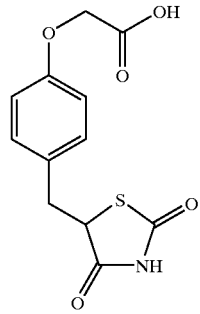

c) condensing the acid of the formula (4) with N-methyl anthranilamide of the formula (7)

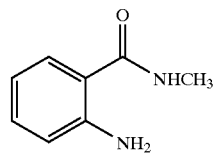

directly without any preactivation of acid to produce the compound of formula (1) and if desired d) preparing a pharmaceutically acceptable salt of formula (1).

2. A process as claimed in claim 1, wherein the compound of the formula (3')

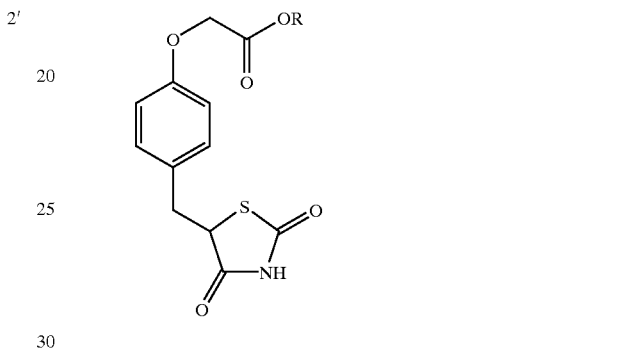

where R is a ($C_1$–$C_4$)alkyl group is condensed directly with N-methyl anthranilamide of the formula (7)

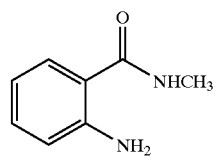

to obtain the compound of the formula (1).

3. A process as claimed in claim 2, wherein the reduction is carried out using Raney Nickel.

4. A process as claimed in claim 3, wherein the reduction is carried out for a period ranging from 8 to 70 hours.

5. A process as claimed in claim 4, wherein the reduction is carried out at a pressure ranging from atmospheric pressure to 41 atmospheric pressure.

6. A process as claimed in claim 5, wherein the reduction is carried out at a temperature in the range of 15° C.–70° C.

7. A process as claimed in claim 6, wherein the purification of the crude reduced product is effected using alcohol containing 1–4 carbon atoms and followed by precipitation using water.

8. A process as claimed in claim 2, wherein the reduction in step (a) is carried out using Mg/alcohol having 1 to 4 carbon atoms.

9. A process as claimed in claim 8, wherein the reduction in step (a) is carried cut using 4 to 12 equivalents of Mg.

10. A process as claimed in claim 9, wherein the temperature of the reaction is in the range of 10° C. to 60° C.

11. A process as claimed in claim 10, wherein the reaction time ranges from 2 to 15 hours.

12. A process as claimed in claim 11, wherein all the magnesium salts are precipitated and filtered off.

13. A process as claimed in claim 1, wherein the reaction time in condensation step (c) ranges from 6 to 20 hours.

14. A process as claimed in claim 2, wherein the reaction time ranges from 5 to 30 hours, preferably ranging from 6 to 20 hours.

15. A process as claimed in claim 2, wherein in step (d) the pharmaceutically acceptable salt is prepared by reacting the compound of formula (1) with methanolic potassium hydroxide, potassium carbonate or potassium t-butoxide in the presence of solvent to yield potassium salt of the compound of formula (1).

16. A process as claimed in claim 15, wherein the addition of methanolic potassium hydroxide or potassium carbonate is carried out at a temperature of 60–70° C.

17. A process as claimed in claim 16, wherein after the addition of potassium hydroxide or potassium carbonate, the reaction mixture is cooled to room temperature and maintained it for 1 h at room temperature.

18. A process as claimed in claim 17, wherein solvent used is selected from xylene/methanol mixture in the ration of 1:1.

19. A process for the preparation of the compound of the formula (2')

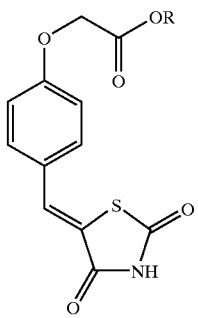

2' where R represents a $(C_1–C_4)$alkyl group, which comprises a) reacting p-hydroxybenzaldehyde of the formula (10)

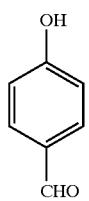

10 with alkylhaloacetate of the formula (11)

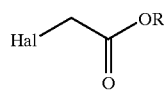

11 where Hal represents a halogen atom or bromine and R is a $(C_1–C_4)$alkyl group using an aromatic hydrocarbon solvent, a base, ally sulphonic acid or aryl sulphonic acid and iodine to obtain the compound of the formula (12)

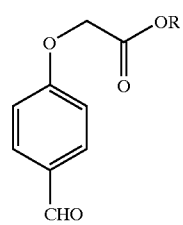

12 and b) condensing the compound of formula (12) where R is as defined earlier with thiazolidine-2,4-dione of the formula (13)

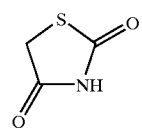

13 in the presence or absence of a solvent using catalysts to produce a compound of formula (2').

20. A process as claimed in claim 19, wherein the aromatic hydrocarbon solvent used is selected from benzene, toluene, xylene or mixtures thereof.

21. A process as claimed in claim 20, wherein the base used is selected from alkali and alkaline earth metal carbonates and bicarbonates such as potassium carbonate, potassium bicarbonate, sodium carbonate or calcium carbonate.

22. A process as claimed in claim 21, wherein the alkyl or aryl sulphonic acid used is selected from methane sulphonic acid, ethane sulphonic acid, propane sulphonic acid, p-toluene sulphonic acid, benzene sulphonic acid or p-nitro benzene sulphonic.

23. A process as claimed in claim 22, wherein the reaction time for step (a) ranges from 3 to 10 hours.

24. A process as claimed in claim 23, wherein the reaction time for step (b) ranges from 6 to 8 hours.

25. A process as claimed in claim 24, wherein the solvent used in step (b) is selected from toluene or xylene.

26. A process as claimed in claim 25, wherein the catalysts used is step (b) are selected from benzoic acid and piperidine.

27. A process as claimed in claim 4, wherein the period ranges from 12 to 24 hours.

28. A process as claimed in claim 5, wherein the pressure ranges to 27 atmospheric pressure.

29. A process as claimed in claim 6, wherein the temperature ranges from 30° C.–60° C.

30. A process as claimed in claim 9, wherein the equivalents are 8 to 10 having 1 to 4 carbon atoms.

31. A process as claimed in claim 10, wherein the range is from 15° C.–30° C.

32. A process as claimed in claim 11, wherein the time ranges from 6 to 8 hours.

33. A process as claimed in claim 23, wherein the time for step (a) ranges from 5 to 7 hours.

34. The process as claimed in claim 1, wherein the reaction times ranges from 10 to 12 hours.

* * * * *